United States Patent
Moeller et al.

(10) Patent No.: US 10,660,346 B2
(45) Date of Patent: May 26, 2020

(54) CAROTENOID COLORING COMPOSITION

(75) Inventors: Jens Moeller, Soeborg (DK); Bjoern Madsen, Helsingoer (DK); Dorthe Lauridsen, Vanløse (DK)

(73) Assignee: CHR. HANSEN NATURAL COLORS A/S, Hoersholm (DK)

( * ) Notice: Subject to any disclaimer, the term of this patent is extended or adjusted under 35 U.S.C. 154(b) by 475 days.

(21) Appl. No.: 14/123,723

(22) PCT Filed: Jun. 4, 2012

(86) PCT No.: PCT/EP2012/060509
§ 371 (c)(1),
(2), (4) Date: Dec. 3, 2013

(87) PCT Pub. No.: WO2012/168189
PCT Pub. Date: Dec. 13, 2012

(65) Prior Publication Data
US 2014/0113027 A1    Apr. 24, 2014

(30) Foreign Application Priority Data

Jun. 6, 2011 (EP) .................................. 11168775

(51) Int. Cl.
| | | |
|---|---|---|
| A23C 19/09 | (2006.01) | |
| A23C 19/05 | (2006.01) | |
| A61K 8/31 | (2006.01) | |
| A61K 8/06 | (2006.01) | |
| A61K 8/11 | (2006.01) | |
| A61Q 1/02 | (2006.01) | |
| A61K 8/73 | (2006.01) | |
| A23C 19/068 | (2006.01) | |
| A23L 33/105 | (2016.01) | |
| A23L 29/219 | (2016.01) | |
| A23L 5/44 | (2016.01) | |

(52) U.S. Cl.
CPC ........ *A23C 19/0925* (2013.01); *A23C 19/054* (2013.01); *A23C 19/0688* (2013.01); *A23L 5/44* (2016.08); *A23L 29/219* (2016.08); *A23L 33/105* (2016.08); *A61K 8/062* (2013.01); *A61K 8/11* (2013.01); *A61K 8/31* (2013.01); *A61K 8/732* (2013.01); *A61Q 1/02* (2013.01); *A61K 2800/882* (2013.01)

(58) Field of Classification Search
CPC .............. A23C 19/0925; A23C 19/054; A23C 19/0688; A23L 1/05223; A23L 1/2753; A61K 8/062; A61K 8/11
USPC .......................................................... 426/40
See application file for complete search history.

(56) References Cited

U.S. PATENT DOCUMENTS

2001/0046546 A1    11/2001    Ernster

FOREIGN PATENT DOCUMENTS

| EP | 1 825 764 A1 | 8/2007 |
|---|---|---|
| GB | 2 248 170 A | 4/1992 |
| WO | WO 99/07233 A1 | 2/1999 |
| WO | WO 2008/110225 A1 | 11/2001 |
| WO | WO 02/41711 A1 | 5/2002 |
| WO | WO-2007/009601 A1 | 1/2007 |
| WO | WO-2007/090610 A2 | 8/2007 |
| WO | WO 2009/007273 A2 | 1/2009 |
| WO | WO-2010/069889 A1 | 6/2010 |
| WO | WO 2010/112406 A1 | 10/2010 |

OTHER PUBLICATIONS

PCT/EP2012/060509, International Search Report, dated Sep. 6, 2012.
Carrie, "Annatto as a Cheese Color," Journal of Dairy Research, vol. 9, pp. 72-79, 1938.
McDonough et al., "Decolorization of Annatto in Cheddar Cheese Whey," Journal of Dairy Science, vol. 51, No. 3, pp. 471-472, 1968.
Croissant et al., "The effect of bleaching agent on the flavor of liquid whey and whey protein concentrate," Journal of Dairy Science, vol. 92, No. 12, pp. 5917-5927, 2009.
Noziere et al., "Carotenoids for ruminants: From forages to dairy products," Animal Feed Science and Technology, vol. 131, pp. 418-450, 2006.
Lück et al., "Colouring Cheese by Means of β-Carotene," South African Journal of Dairy Technology, vol. 4, No. 4, pp. 207-213, 1972.
Lück et al. "Problems Encountered With the Colouring of Cheese by Means of "Water-Soluble" β-Carotene Preparations," South African Journal of Dairy Technology, vol. 5, No. 4, pp. 181-185, 1973.
Chapman et al., "The use of carotenoid preparation for colouring Cheddar cheese," Journal of Society of Dairy Technology, vol. 33, No. 4, pp. 162-164, 1980.
Kang et al., "Invited review: Annatto usage and bleaching dairy foods," Journal of Dairy Science, vol. 93, No. 9, pp. 3891-3901, 2010.
Morganti et al., "Lutein as skin nutrient," Chemical Abstracts Service, Dec. 2007 (Abstract).
Supplementary European Search Report dated Nov. 28, 2011 in application No. EP 11 16 8775.

*Primary Examiner* — Jeffrey P Mornhinweg
(74) *Attorney, Agent, or Firm* — Foley & Lardner LLP

(57) ABSTRACT

The present invention relates to a composition for coloring foods, beverages, animal feeds, cosmetics or drugs comprising 1) dissolved carotenoid emulsified as an oil-in-water emulsion using a suitable emulsifier and 2) crystalline carotenoid encapsulated in a suitable hydrocolloid, making it water-dispersible and thereby miscible with the oil-in-water emulsified carotenoid fraction, mixed in a ratio of between 1:100 to 100:1. The present invention further relates to a method for preparing the coloring composition, a method for preparing a food, beverage, animal feed, cosmetic or drug and a food, beverage, animal feed, cosmetic or drug comprising the coloring composition.

19 Claims, 6 Drawing Sheets

CAROTENOID COLORING COMPOSITION

CROSS-REFERENCE TO RELATED APPLICATIONS

This application is a national phase of international application PCT/EP2012/060509, filed Jun. 4, 2012, which was published on Dec. 13, 2012, as WO 2012/168189, which claims the benefit of European application No. 11168775.2, filed Jun. 6, 2011. The respective contents of these applications are incorporated here by reference in their entirety.

FIELD OF THE INVENTION

The present invention relates to a composition for coloring foods, beverages, animal feeds, cosmetics or drugs comprising 1) dissolved carotenoid emulsified as an oil-in-water emulsion using a suitable emulsifier and 2) solid carotenoid particles encapsulated in a suitable hydrocolloid, making it water-dispersible and thereby miscible with the oil-in-water emulsified carotenoid fraction, mixed in a ratio of between 1:100 and 100:1. The present invention further relates to a method for preparing the coloring composition, a method for preparing a food, beverage, animal feed, cosmetic or drug and a food, beverage, animal feed, cosmetic or drug comprising the coloring composition.

BACKGROUND OF THE INVENTION

It was in Southern England in a place called Cheddar that it was found that the natural carotene color in milk was carried through to the cheese curd in high levels during the summer month when the cows were feeding on fresh grass and in lower levels during fall and winter when the cows were fed hay. Thus, the natural color of cheese varied over the course of a year and the visual aspect of the color became important in terms of consumer perception of the quality of cheddar cheese.

Cheese makers then started to add coloring agents. Traditionally, the most common of these is annatto, a yellow-red dye made from the seeds of the *Bixa orellana* tree (Carrie, 1938). The pigments of annatto are two carotenoids; the fat soluble part of the crude extract is called bixin the water-soluble part is called norbixin.

Dyeing the cheeses eliminates seasonal color fluctuations and the use of annatto color is extremely important to achieve the visual appearance of colored cheese, including cheddar, Leicester, Gloucester, etc.

The whey obtained during the cheese process contains significant level of proteins, and in order to be able to valorize this protein, various harsh chemical treatments have been suggested (McDonough et al., 1968), and these all impose undesirable traits for the whey protein, e.g. oxidized flavor, impaired nutritional value and generation of unwanted yellowish color due to oxidation products (Croissant et al., 2009).

A number of carotenoids are found naturally in cows milk, i.e. lutein, violaxanthin, antheraxanthin, zeaxanthin, neoxanthin, all-trans beta-carotene, alpha-carotene, and 13-cis beta-carotene, and among those, lutein and beta-carotene are the most abundant quantitatively (Noziere et al., 2006).

An overall trend within food products is a wish for the products to contain ingredients which are already in the products in nature. Because of the consumer preferences and issues regarding quality or utility of the whey fraction following use of annatto as colorant (Kang et al., 2010), the use of carotenoids, and especially beta-carotene, to color food, particularly cheese, has been researched (Lück and Downes, 1972; Luck, 1973; Chapman et al., 1980).

Beta-carotene is a useful cheese coloring agent because it is naturally present in milk, it gives cheese a color which appeals to the customer and it does not produce off-flavors during the ripening of the cheese.

The use of beta-carotene to color cheese is advantageous over annatto in that the chemical compound may be more closely controlled than the natural product. Beta-carotene may be synthesized or extracted from natural sources. Additionally, discovered health benefits of beta-carotene further promote the use of the substance over annatto.

Processing of some milk products (e.g. cheese and butter) involves selective transfer of constituents from milk to milk products. Given that carotenoids and retinol are fat-soluble, they mainly behave like milk fat (Noziere et al., 2006).

However, beta-carotene, and especially annatto, preparations face the problem that a large amount of color is lost in the whey during the cheese making process.

GB 2248170 uses emulsified beta-carotene with caseinate as ingredient thereby claiming that the beta-carotene is better trapped in the cheese curd and not transferred to the whey fraction.

WO 99/07233 relates to producing a uniform coloration in cheese by associating a food grade colorant, such as beta-carotene, with a carrier, such as caseinate, which is then dispersed within the milk source that is processed into a final cheese product.

US 2001/0046546 relates to a mixture of synthetic carotenal (carotenoid containing an aldehyde functional group) and natural beta-carotene in butter oil (anhydrous milk fat), as a carrier, for use as a colorant in food products, such as processed cheese.

Other patent documents are related to increasing the carotenoid concentration by using a hydrocolloid as a carrier or matrix.

WO 2007/009601 is directed to a composition comprising at least one carotenoid, such as beta-carotene, which is dispersed in a matrix containing at least one starch and/or modified starch.

WO 2008/110225 relates to compositions comprising gum acacia and at least one carotenoid for coloration of food, beverages, animal feed, cosmetics or pharmaceutical compositions.

WO 2010/112406 is directed to a stable suspension of partially amorphous carotenoid particles, comprising 1 to 20% (w/w) of at least one carotenoid, such as beta-carotene, 0.2% (w/w) to 20% (w/w) of an edible oil, 3% (w/w) to 60% (w/w) of a hydrophilic protective colloid, 5% (w/w) to 60% (w/w) of a physiologically suitable polyalcohol and 5% (w/w) to 60% (w/w) of water.

Nevertheless, an attempt to match the color shade of annatto, norbixin, using beta-carotene for certain cheddar cheeses has not been successful, and authors state that final color shade using beta-carotene is too yellow compared to that of annatto (Chapman et al., 1980).

Therefore, paprika has been used in combination with beta-carotene to provide a finished cheese product with the same color as annatto-colored cheeses.

WO 2010/069889 relates to a composition for coloring cheese curd comprising a combination of an oil phase comprising an effective amount of paprika, an effective amount of a carotenoid, and a fat, and an aqueous phase comprising a caseinate.

Thus, there is a need for alternative and improved beta-carotene coloring compositions that prevents coloration of the whey by-product stream, while simultaneously providing a finished cheese product with the same color as annatto-colored cheese.

SUMMARY OF THE INVENTION

The aim of the present invention is to provide an alternative pigment composition using a carotenoid for coloring of foods, such as cheeses, beverages, animal feeds, cosmetics or drugs. Especially, it is an aim of the present invention to provide an improved coloring composition comprising beta-carotene which is capable of matching the annatto color in cheese.

The solution is based on creating a liquid coloring composition containing both carotenoid in an oil-in-water emulsion and carotenoid particles encapsulated with a hydrocolloid.

As can be seen in the Examples herein, the solution was surprisingly found to provide a very good coloration of cheese and a color shade which was able to match that of annatto in cheese.

Thus, a first aspect of the present invention relates to a liquid coloring composition comprising a) carotenoid dissolved in an oil phase wherein the oil phase is emulsified in an aqueous phase using a suitable emulsifier and b) water dispersible carotenoid particles encapsulated with a suitable hydrocolloid, wherein the oil phase is present in an amount of between 3% (w/w) to 40% (w/w) of a), the hydrocolloid is present in an amount of at least 5% (w/w) of b), the ratio of a):b) is between about 1:100 to about 100:1, and the total carotenoid content of a) and b) is between about 0.1% (w/w) to about 15% (w/w) of the resulting liquid coloring composition.

A second aspect of the present invention relates to a method for preparing a liquid coloring composition comprising the steps of:
a) preparing an oil-in-water emulsion of a dissolved carotenoid using a suitable emulsifier by i) preparing an aqueous phase; ii) preparing an oil phase by heating a fat comprising the carotenoid to a temperature suitable for dissolving the carotenoid; and iii) mixing the oil phase in the aqueous phase;
b) preparing a formulation of carotenoid particles encapsulated in a suitable hydrocolloid by milling carotenoid particles in the presence of a suitable hydrocolloid; and
c) mixing the oil-in-water emulsion of a) with the encapsulated carotenoid particle formulation of b) in a ratio a):b) of between about 1:100 and about 100:1.

A third aspect of the present invention relates to a method of coloring cheese comprising the steps of:
a) adding a starter culture, rennet and the liquid coloring composition according to the first aspect of the present invention to milk;
b) incubating the mixture under conditions favorable to the generation of curd and whey fractions, and
c) separating the curds from the whey.

A fourth aspect of the present invention is directed to a food product, a beverage, an animal feed, a cosmetic or a drug comprising the liquid coloring composition according to the first aspect of the present invention.

A fifth aspect of the present invention relates to use of the liquid coloring composition according to the first aspect of the present invention as a colorant for foods, beverages, animal feeds, cosmetics or drugs.

DETAILED DESCRIPTION OF THE INVENTION

Definitions

The term "pigment" relates to a material that changes the color of light it reflects as the result of selective color absorption. This physical process differs from fluorescence, phosphorescence, and other forms of luminescence, in which the material itself emits light.

The term "carotenoid" as used herein comprises carotenes or structurally related polyene compounds, such as xanthophylls, which can be used as a colorant for foods, beverages, animal feeds, cosmetics or drugs. Examples of such carotenoids are alpha- or beta-carotene, 8'-apo-beta-carotenal, 8'-apo-beta-carotenoic acid esters such as ethyl ester, canthaxanthin, astaxanthin, lycopene, lutein, zeaxanthin or crocetin, or mixtures thereof. As already mentioned, the preferred carotenoid is beta-carotene.

Implementation and Aspects of the Invention

The liquid coloring composition of the present invention is made up of 2 main fractions:
a) an emulsified carotenoid (oil-in-water emulsion) formulation and ii) a formulation with water dispersible carotenoid particles encapsulated with a hydrocolloid.

In a preferred embodiment of the present invention the ratio of a):b) is between about 1:100 to about 100:1, such as between about 1:10 to about 10:1, such as between about 1:5 to about 5:1.

Carotenoids from natural sources as well as their nature-identical counterparts may be used.

In a preferred embodiment of the present invention, the coloring composition is made with the following carotenoids: beta-carotene, alpha-carotene, gamma-carotene, zeaxanthin, lutein and cis/trans isomers thereof.

In an even more preferred embodiment the carotenoid is beta-carotene.

As emulsifier one of the following may be used: lecithin, caseinate, such as sodium caseinate, calcium caseinate or acid casein, citric acid esters, mono-/di-glycerides, polyoxyethylene sorbitan fatty acid esters or a hydrocolloid, e.g. milk and pea proteins or acacia gum, and it can be added either to the oil phase or water phase depending on its solubility.

Preferably, the amount of emulsifier used in the oil-in-water emulsion is from about 1% weight per weight to about 20% weight per weight, such as from about 2% weight per weight to about 10% weight per weight.

Ascorbyl palmitate may be added to regenerate antioxidants present at the emulsion interface.

Other ingredients in the water phase may include sugar, starches and organic acids.

Preferably, the oil phase comprises a fat selected from the group consisting of lard, butter or a vegetable oil, such as sunflower seed oil, corn oil, soybean oil, olive oil, coconut oil, palm oil, palm kernel oil, groundnut oil, cottonseed oil, grapeseed oil, rapeseed oil or medium-chain triglyceride oil, and combinations thereof.

The amount of fat used in the oil-in-water emulsion may be between about 0.5% weight per weight to about 50% weight per weight, preferably about 10% weight per weight to about 20% weight per weight.

Antioxidants, preferable alpha-tocopherol or mixed tocopherols, may be added to the oil phase in order to protect carotenoids during heating and subsequently stabilize the final color formulation against oxidative degradation.

Antimicrobials such as organic acids or salts thereof, e.g. sorbic acid, benzoic acid, may be used to inhibit growth of microorganisms during storage.

Preferably, the composition further comprises an emulsion stabilizer. Suitably, the emulsion stabilizer may be selected from the group consisting of maltodextrin, sucrose, glucose, fructose, lactose, maltose, invert sugar, and combinations thereof.

The carotenoid particles may comprise amorph carotenoid as well as crystalline carotenoid. Preferably, the carotenoid particles comprise 100% crystalline carotenoid.

In a preferred embodiment the amount of hydrocolloid in the milled fraction is at least about 0.5% weight per weight, such as at least about 5% weight per weight.

Other additives may be carbohydrates such as glucose syrup, dextrose or sugar, or organic acids, antioxidants and antimicrobials.

Preferably, the total beta-carotene pigment content is from about 0.1% weight per weight to about 15% weight per weight, more preferably from about 0.5% weight per weight to about 10% weight per weight.

The process of preparing the coloring composition comprises three steps:

Firstly, an oil-in-water emulsion of a dissolved carotenoid is prepared using a suitable emulsifier by i) preparing an aqueous phase; ii) preparing an oil phase by heating a fat comprising the carotenoid to a temperature suitable for dissolving the carotenoid; and iii) mixing the oil phase in the aqueous phase by stirring;

The term "a temperature suitable for dissolving the carotenoid" refers to a temperature in a range from about 120° C. to about 230° C., at which temperature the carotenoid can be dissolved in the fat during the process of preparing the oil-in-water emulsion.

In a preferred embodiment, the temperature suitable for dissolving the carotenoid is between about 140° C. to about 160° C.

The two phases are mixed using high speed propeller stirring, and the subsequent processing step is an emulsification by either high-shear rotor-stator or a high-pressure two stage homogenizer. A particle size distribution with an average particle size in the range 0.25-2.50 µm is obtained following the emulsification of this fraction.

Secondly, a fraction containing water-dispersible, encapsulated particles of carotenoid is produced by milling the carotenoid particles either in dry form or as a water suspension with a hydrocolloid, such as non-modified starch or modified starch, milk or pea protein or beet pectin, thereby stabilizing the suspension of the encapsulated carotenoid in aqueous phase and avoiding slow dissolution of particles in presence of oily phases.

The suspension is heated moderately, e.g. to 55° C., while mixing by high speed propeller stirring and a pre-emulsification using a rotor-stator high-shear mixer for a short time period. The suspension is thereafter submitted to ball mill step in order to increase the surface area of the particles while simultaneously ensuring coverage of particles with stabilizing hydrocolloid.

The third and final step is to mix the emulsion fraction and the milled fraction by stirring. It is also possible to mix ratios that ensure a desired reddish shade in the final application.

As mentioned above, an aspect of the present invention relates to a food product, a beverage, an animal feed, a cosmetic or a drug comprising the coloring composition according to the present invention.

In a preferred embodiment, the food product is a cheese, such as a traditional cheese or a processed cheese.

The coloring composition of the present invention may find use as a colorant for cheese, such as traditional cheese or processed cheese.

The coloring composition of the present invention may find use as colorant not only for cheese but also for other foods, beverages, animal feeds, cosmetic and drugs.

As will be appreciated by the skilled person, the coloring composition of the present invention may be added either as an aqueous stock solution or a pre-blend with other suitable food ingredients according to the specific application. Mixing may be carried out e.g. using a low shear mixer, a high pressure homogenizer or a high shear mixer depending on the formulation of the final application. Mixing procedure and amount of oily or aqueous ingredients may impact the color of the final application. As will be readily apparent such technicalities are within the skill of the expert.

Embodiments of the present invention are described below, by way of non-limiting examples.

EXAMPLES

Example 1—Match of Annatto Colorant in Fresh Cheese Curd

Formulation of Samples:

Ingredients used were: Demineralized water, 30% beta-carotene (sourced from BASF SE), beta-carotene crystals powder (sourced from Zhejiang NHU Company Ltd.), non-modified starch (sourced from Roquette), calcium caseinate (sourced from Arla Foods), sucrose (sourced from Nordic Sugar), ascorbyl palmitate (sourced from DSM), medium-chain triglycerides (MCT) oil (sourced from Stern Chimie), sunflower oil (sourced from Bressner), lecithin (sourced from Cargill), natural tocopherols (sourced from Cognis).

List of ingredients for the two fractions is shown in Table 1 and 2.

TABLE 1

| List of materials for emulsified beta-carotene fraction | |
|---|---|
| Ingredients (BATCH 5624-134) | % |
| Water phase | |
| Non-modified Starch | 2.5 |
| Calcium Caseinate | 7.5 |
| Sucrose | 20 |
| Ascorbyl Palmitate | 1 |
| Water | 48 |
| Oil phase | |
| 30% BC | 4 |
| Mixed tocopherol | 1.75 |
| Sunflower Lecithin | 1.5 |
| MCT oil | 7 |
| Sunflower oil | 6.75 |
| | 100 |

TABLE 2

List of materials for milled beta-carotene fraction

| Ingredients (BATCH 5624-133) | % |
|---|---|
| Water | 63.0 |
| Glucose syrup | 30.0 |
| Non-modified starch | 5.9 |
| beta-carotene crystals (100%) | 1.1 |
| | 100.0 |

The processing steps for the emulsified fraction are:
1. Prepare the aqueous phase by adding sugar, non-modified starch, calcium caseinate and ascorbyl palmitate to heated water solution. Heat during stirring to 55° C. until the ingredients are dissolved
2. Heat the oil phase components; sunflower oil, MCT, alpha-tocopherol, lecithin and beta-carotene to approx. 145° C. making sure all crystals are melted
3. Transfer the oil phase into the water phase while strong stirring ensuring vortex in mixed liquids. Monitor temperature during mixing
4. Emulsify the mixture using an Ultra-Turrex at maximum speed for 1 min making sure that the mixing is performed throughout the entire liquid mixture
5. Allow the emulsion to cool to room temperature The processing steps for the milled fraction are:
1. A water phase with added glucose syrup, non-modified starch is heated to 55° C. while mixing by propeller stirring
2. beta-carotene crystals are added and mixed gradually into the suspension using high speed propeller stirring
3. An Ultra-Turrex is used to make a uniform distribution of crystals in the water phase and a rotor-stator high-shear mixer for a short time period.
4. The suspension is milled on a FrymaKoruma MS-12 stirrer bead mill (Rheinfelden, Switzerland) having a chamber volume of 0.492 L with ball filling degree of 75%. The balls used is ceramic sintered zirconium silicate, type ZS, with a diameter 0.6-0.8 mm (Sigmund Lindner GmbH, Warmensteinach, Germany). The milling process is carried out with a flow rate of approx. 5 L/h, mill speed 4-5 and the mill current is 4.5 volts and temperature approx. 25° C.

As the final step a simple mixing of the emulsion fraction and the milled fraction by stirring while adding ratios that ensure the desired reddish shade in the final application.

The strengths of pigment in the two fractions are determined in water suspension followed by extracting/dissolving beta-carotene in acetone at appropriate dilution. An extinction coefficient, $E_{1\ cm}^{1\%}$, of 2559 at $\lambda$=452 nm is used to determine the concentration of beta-carotene (w/w %). Strengths of beta-carotene are found to be 0.97% and 0.98% for the emulsified fraction and the milled fraction, respectively.

Figure 1:
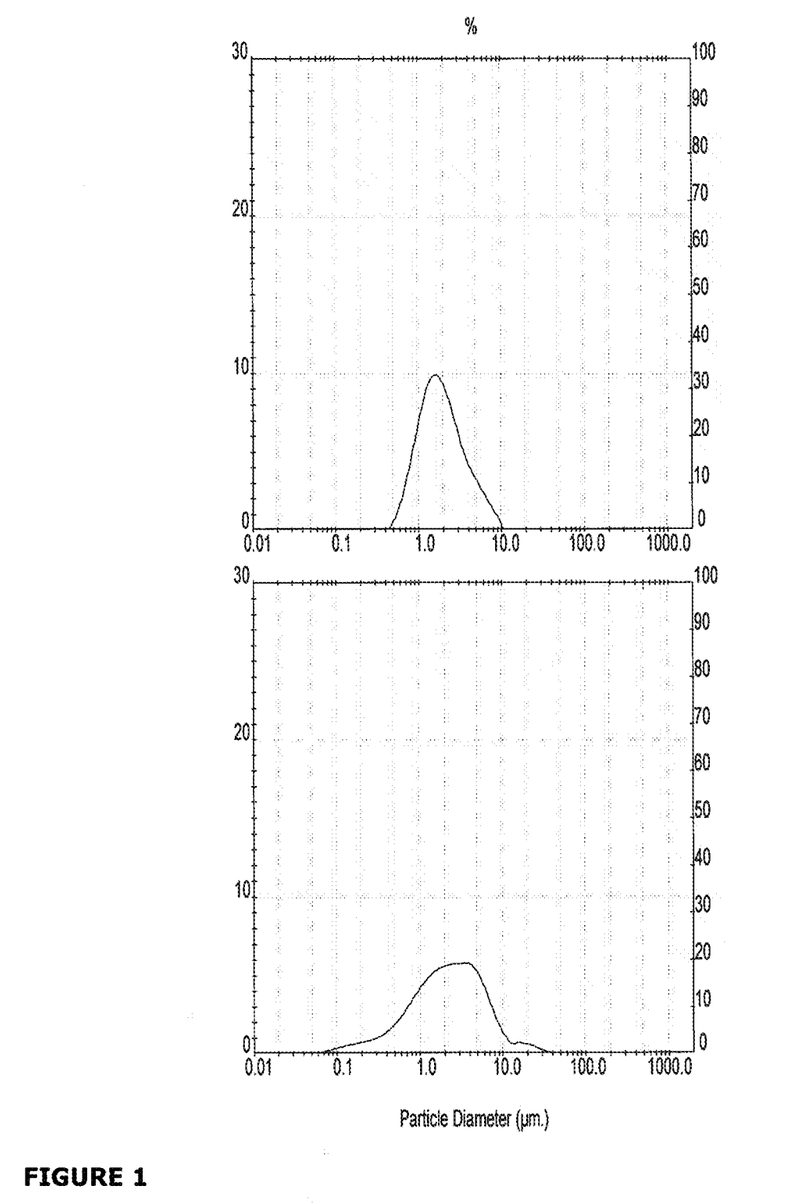
FIG. 1 shows particle size distribution curves for emulsified (top) and milled beta-carotene (bottom).

FIG. 1 shows particle size distributions of the two fractions. The average particle sizes, D(v,0.5), are 1.81 μm and 2.21 μm for the emulsified and milled fraction, respectively.

Application Tests in Fresh Cheese Curd

An application test was conducted in order to test the ability of a beta-carotene color (two separate fractions) to match annatto in fresh cheese.

Colors studied (and pigment content in parentheses):
Annatto: A-320-WS (1.1%) from Chr. Hansen
Emulsified beta-carotene (0.97%) 5624-134—("Emulsified BC" hereafter)
Milled, crystalline beta-carotene (0.98%) 5624-133—("Milled BC" hereafter)

Ingredients: Pasteurized, unhomogenized whole milk (3.5% fat), starter culture, F-DVS-CHN-19 (obtainable from Chr. Hansen, Denmark), and rennet, ChyMax™ Plus (obtainable from Chr. Hansen, Denmark).

Instruments: spectrocolorimeter: SPECTRAFLASH SF 450 (DataColor, Lawrenceville, N.J., USA) and water bath set at 32.5° C. and 38° C., respectively.

In the procedure for making lab scale cheese, 4 vats can be made at a time. The beta-carotene products are tested to match in the final cheese the use of A-320-WS at approx. 1.3 ppm norbixin in the cheese milk. The semi-hard cheeses (Havarti-type), are made according to following procedure:

1. 4 cheese vats containing 2000 g milk each, are placed in the water bath at 32.5° C.
2. Color is added according to recipe.
3. The starter culture (0.24 g culture/2000 g milk— Culture Pre-blend: Add 2.4 g Culture to 100 g milk. Stir to secure a homogenous distribution of the bacteria. Add 10 g of the pre-blend to each cheese vat.) is added during stirring for 1 min, so that a homogenous distribution of bacteria is secured. Left for maturation in 30 min.
4. Rennet (500 μl/2000 g milk) is added, stirred for 1 min. and left for 40 min. with lid.
5. The firmness of the cheese curd is checked and the cheese is cut with the special grid knife.
6. Gentle stirring for approx 8-10 min.
7. Approx. 4×200 ml tap water is heated to 80° C.
8. Approx. 400 g whey is removed from the cheese vat. Use a rubber tube to lift up the whey through a cheese cloth. L*a*b*-readings on the whey samples.
9. The water bath is adjusted to 38° C. and 2×100 ml 80° C. tap water is added to the cheese vat during the next 30 min (100 ml pr 15 min). The water is slowly added in the middle of the vat while stirring. End temperature should be 36-38° C.
10. When reaching a temperature of 36-38° C., the stirring is to be continued for 5 min.
11. The cheese grains and whey is poured into a sieve placed on a glass beaker. The sieve is to be covered with cheese cloth. Leave it under 2 kg pressure (glass beaker with water) for 15 min.

Table 3 gives an overview over the different cheese vats including type and ratio of colorant added.

TABLE 3

Overview of lab cheese vats and color formulations and strengths applied.

| VAT No. | Product | Batch | Strength (%) | ppm | BC Ratio |
|---|---|---|---|---|---|
| 1 | A-320-WS | 2971417 | 1.1 | 1.29 | — |
| 2 | Emulsified BC/ Milled BC | 5624-134/5624-133 | 0.97/0.98 | 2.00/ 0.33 | 86%:14% |
| 3 | Emulsified BC/ Milled BC | 5624-134/5624-133 | 0.97/0.98 | 2.00/ 0.70 | 74%:26% |
| 4 | Emulsified BC/ Milled BC | 5624-134/5624-133 | 0.97/0.98 | 2.00/ 1.00 | 67%:33% |

Color measurements made in reflectance mode carried out on the DataColor SF450, LAV opening (calibrated to a white tile) on cheese milk added colorant.

TABLE 4

Tristimulus L*a*b* values of color formulations in cheese milk:

| Sample name | L* | a* | b* | C* | H* | ΔL* | ΔC* | ΔH* | ΔE* | CIE2000 ΔE |
|---|---|---|---|---|---|---|---|---|---|---|
| Vat 1, 1.3 ppm A-320 | 86.63 | 3.07 | 20.02 | 20.26 | 81.29 | | | | | |
| Vat 2, 2 + 0.33 ppm BC | 87.37 | 2.31 | 16.11 | 16.28 | 81.85 | 0.74 | −3.98 | 0.18 | 4.05 | 2.27 |
| Vat 3, 2 + 0.70 ppm BC | 87.03 | 2.93 | 15.96 | 16.22 | 79.59 | 0.40 | −4.03 | −0.54 | 4.09 | 2.29 |
| Vat 4, 2 + 1.00 ppm BC | 86.62 | 3.38 | 15.78 | 16.14 | 77.92 | −0.01 | −4.12 | −1.06 | 4.25 | 2.51 |

The L*a*b* values are determined by DataColor spectroflash SF450

To illustrate the difference in color for two samples the distance between colors can be evaluated. When the term CIE2000 ΔE is applied a rule of thumb says that a value >2 can clearly be observed visually while a value in the range 1-2 is a match and a value <1 means that samples cannot be differentiated visually.

The initial appearance of the tested colors in cheese milk shows that all vats with beta-carotene lack chroma. Vat 4 with the highest dosage of beta-carotene has a L*value; and vat 2 with the lowest dosage of beta-carotene has a hue value that is closest to the dosage of annatto. Vat 2 and vat 3 with intermediate dosages of beta-carotene have higher L*values, so initially it could appear that the dosage of total beta-carotene is too low.

However, this may change by the end of cheese processing when evaluating the cheese and whey samples, since beta-carotene is retained to a much higher degree in the cheese curd.

Table 5 and 6 show tristimulus color values obtained from reflectance mode measurement with DataColor 450 on the whey obtained as drainage after step 8 and as the final drain at step 11.

TABLE 5

Tristimulus L*a*b* values of whey from drain 1 (step 8)

| Sample name | L* | a* | b* | C* | H* | ΔL* | ΔC* | ΔH* | ΔE* | CIE2000 ΔE |
|---|---|---|---|---|---|---|---|---|---|---|
| Vat 1, 1.3 ppm A-320 | 66.61 | −1.69 | 17.29 | 17.37 | 95.59 | | | | | |
| Vat 2, 2 + 0.33 ppm BC | 68.43 | −3.34 | 12.80 | 13.23 | 104.64 | 1.82 | −4.15 | 2.39 | 5.12 | 3.88 |
| Vat 3, 2 + 0.70 ppm BC | 68.41 | −3.18 | 12.92 | 13.30 | 103.82 | 1.81 | −4.07 | 2.18 | 4.96 | 3.69 |
| Vat 4, 2 + 1.00 ppm BC | 67.72 | −3.11 | 12.77 | 13.14 | 103.71 | 1.11 | −4.23 | 2.14 | 4.87 | 3.55 |
| Vat 0, blind control | 66.71 | −4.15 | 10.84 | 11.60 | 110.95 | 0.10 | −5.77 | 3.79 | 6.90 | 5.38 |

The L*a*b* values are determined by DataColor Spectroflash SF450

TABLE 6

Tristimulus L*a*b* values of whey from final drain (step 11)

| Sample name | L* | a* | b* | C* | H* | ΔL* | ΔC* | ΔH* | ΔE* | CIE2000 ΔE |
|---|---|---|---|---|---|---|---|---|---|---|
| Vat 1, 1.3 ppm A-320 | 55.33 | −2.11 | 12.48 | 12.66 | 99.60 | | | | | |
| Vat 2, 2 + 0.33 ppm BC | 57.82 | −3.26 | 9.71 | 10.24 | 108.55 | 2.50 | −2.42 | 1.78 | 3.90 | 3.44 |
| Vat 3, 2 + 0.70 ppm BC | 56.78 | −3.24 | 9.33 | 9.88 | 109.15 | 1.45 | −2.79 | 1.86 | 3.65 | 3.08 |
| Vat 4, 2 + 1.00 ppm BC | 57.57 | −3.00 | 9.72 | 10.17 | 107.16 | 2.24 | −2.49 | 1.50 | 3.67 | 3.12 |
| Vat 0, blind control | 56.62 | −4.08 | 7.69 | 8.71 | 117.96 | 1.29 | −3.95 | 3.35 | 5.34 | 4.64 |

The L*a*b* values are determined by DataColor Spectroflash SF450

The L*a*b* values from vat 0, blind control, originates from a previous Lab cheese test (T2010-333) and these values are only indicative, since there may exist smaller changes in the L*a*b* readings from different lab cheese runs due to differences in cheese milk composition, starter culture and rennet.

It is very clear that all combinations of beta-carotene, vat 2-4, both for drain 1 and final drain exhibit less color transfer to the whey compared to the vat produced with annatto as colorant, e.g. illustrated both by differences in chroma and ΔE values.

Figure 2:
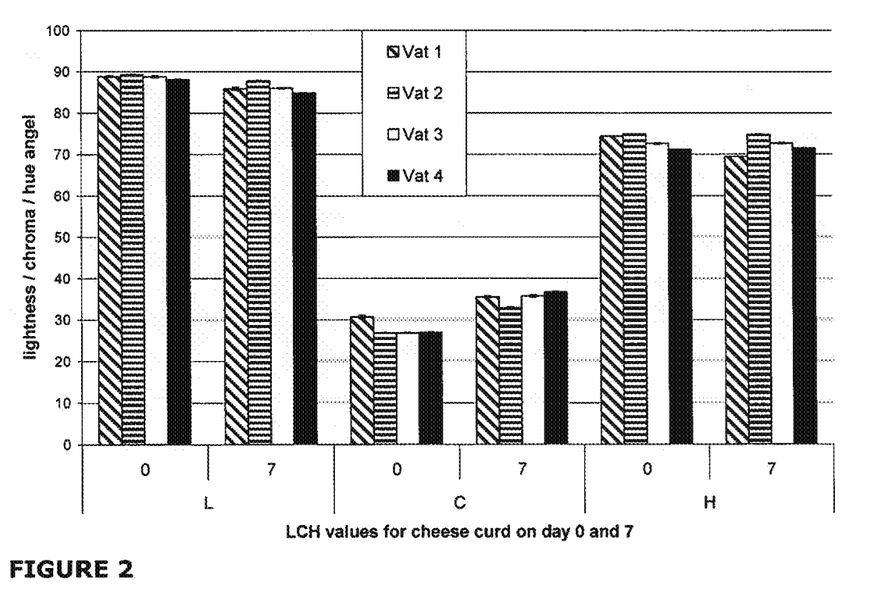
FIG. 2 depicts a bar plot showing tristimulus values for lightness, chroma and hue angel of cheese curds added annatto (vat 1), milled, crystalline to emulsified beta-carotene at ratios: 0.17 (vat 2); 0.35 (vat 3) and 0.50 (vat 4) on day 0 and 7.

The LCH values in FIG. 2 are based on readings from duplicate cheeses and standard deviations indicated by the error bars illustrate that a very good agreement between two genuine replicates is observed.

On day 0 all fresh cheese curds with added beta-carotene have lower chroma than cheese curd with added annatto. The combination Emulsified BC 2.0 ppm and Milled BC 0.33 ppm is initially the cheese closest to annatto, while the other ratios tested all have more orange-red hue's.

At day 7 the cheese with added annatto has slightly more orange red hue than all the tested BCs. Regarding L*value and chroma the combination of Emulsified BC with 2.0 ppm and Milled BC with 0.70 ppm is the one most similar in appearance to the cheese with annatto as colorant, and the resulting values for CIE2000 ΔE relative to annatto is 1.54, which signifies a good match. Likewise, the combination of 2.0 ppm Emulsified BC with 1.0 ppm Milled BC also shows good resemblances to cheese with added annatto, especially regarding chroma and hue angel having CIE2000 ΔE of 1.21 approaching a variation in overall color shade that can hardly be detected by the human eye.

Example 2—Ratio of Emulsified and Crystalline Beta-Carotene Controls Color Shade This example illustrates how color shade, i.e. between yellowish toward reddish tones, can be controlled by varying the ratio between emulsified beta-carotene and milled, crystalline beta-carotene, which makes it possible to match reddish shade of annatto and go even beyond.

Emulsified BC fraction—Ingredients used were: Demineralized water, 30% beta-carotene (sourced from BASF SE), sucrose (sourced from Nordic Sugar), ascorbyl palmitate (sourced from DSM), alpha-tocopherol (sourced from BASF SE) and citric acid esters (sources from Danisco).

Milled crystalline BC (CC Red ID 500)—Ingredients used were: citric acid (sourced from Gadot Biochemical Industries Ltd.), potassium sorbate (sourced from Daicel Nanning Food Ingredients), Glycerol (sourced from Cremer Oleo), Modified starch from waxy maize (sourced from National Starch), beta-carotene crystals (100%)

TABLE 8

List of materials for emulsified beta-carotene (BATCH 2972079)

| Ingredients | % |
| --- | --- |
| Water phase | |
| Sugar | 35 |
| Citric Acid Esters of mono-and diglycerides (Citrem N-12) | 2 |
| Tap Water | 32 |
| Oil phase | |
| 30% BC | 5 |
| Ascorbyl palmitate | 0.1 |
| alpha-tocopherol | 0.9 |
| Sunflower oil | 25 |
| | 100 |

TABLE 7

Visual inspection of color intensity[a] of whey and cheese curd at 2 stages of processing

| Vat no. | Product | Dosage (%) | Concentration (ppm) | Color of whey 1st drain | Color of whey Final drain | Color of cheese curd day 0 | Color of cheese curd day 7 |
| --- | --- | --- | --- | --- | --- | --- | --- |
| 1 | Annatto, A-320-WS | 0.0118 | 1.29 | ++ | + | ++ | ++ |
| 2 | Emulsified BC + Milled BC | 0.0206/0.0034 | 2.00/0.33 | + | (+) | (++) | (++) |
| 3 | Emulsified BC + Milled BC | 0.0206/0.0072 | 2.00/0.70 | + | (+) | (++) | ++ |
| 4 | Emulsified BC + Milled BC | 0.0206/0.0102 | 2.00/1.00 | + | (+) | (++) | (+++) |

[a]symbols used to grade color intensity: −: no color, +: almost no color, ++: medium colored, +++: intensely colored All combinations of Emulsified BC and Milled BC investigated herein remain almost completely within the cheese matrix. However, initially samples with added combinations of Emulsified BC and Milled BC possess a more orange/red hue and have much lower chroma compared to that of annatto.

After storage for 7 days the combination of Emulsified BC (5624-134) with 2.00 ppm combined with Milled BC (5624-133) with 0.70 ppm or 1.00 ppm have a performance in the cheese curd close to that of 1.29 ppm A-320-WS. These cheeses with added beta-carotene have a color shade that cannot be visually differentiated from that of standard color annatto product, A-320-WS, applied at 1.3 ppm.

Processing steps in producing the emulsified beta-carotene 2 formulation.

1. The oil phase is heated and maintained at 140° C., while the ingredients beta-carotene and ascorbyl palmitate are added during mixing 2. The water phase is heated to 50° C. before sugar and emulsifier, citric acid esters, are added.
3. The water phase is set at 90° C. before the oil phase is mixed into the water phase
4. A two-stage homogenization is carried out using a pressure of 230 bar and a back-pressure of 30 bar.
5. A final heat treatment to 90° C. is carried out followed by cooling to 30-35° C. and filtration through a 150 μm filter.

TABLE 9

List of materials for milled beta-carotene crystals (BATCH 2946953)

| Ingredients | % |
|---|---|
| Water | 29.8 |
| citric acid | 0.1 |
| potassium sorbate | 0.1 |
| Glycerol | 44.0 |
| Modified starch from waxy maize | 16.0 |
| beta-carotene crystals (100%) | 10.0 |
| SUM | 100.0 |

The process for producing the milled crystalline beta-carotene composition is as follows:
1) Water and modified starch is added and mixed by Silverson mixer
2) Glycerol, citric acid and potassium sorbate are added and stirring is continued until all starch has been dissolved
3) beta-carotene crystals are added gradually at fast stirring while allowing all powder to be wetted. Silverson mixing is performed to ensure uniform suspension of crystals in the water/starch
4) The water phase is stirred with propeller while heating to 65° C.; all ingredients are added slowly and dissolved
5) Before milling control of suspension is carried out with respect to $a_w<0.80$ and pH in the range 5.5-6.5. If pH is out of this range either citric acid or trisodium citrate can be used to adjust pH
6) The suspension is milled on a FrymaKoruma MS-12 stirrer bead mill (Rheinfelden, Switzerland) having a chamber volume of 0.492 L with ball filling degree of 60%. The balls used is ceramic sintered zirconium silicate, type ZS, with a diameter 0.6-0.8 mm (Sigmund Lindner GmbH, Warmensteinach, Germany). The milling process is carried out with a flow rate of approx. 5 L/h, mill speed 4-5 and the mill current is 4.5 volts and temperature approx. 25° C.
7) The product is filtrated through a 250 μm filter at 25-30° C.

The beta-carotene strengths of these compositions are 1.48% and 10.40% for the emulsified and milled crystalline fraction, respectively.

Figure 3:
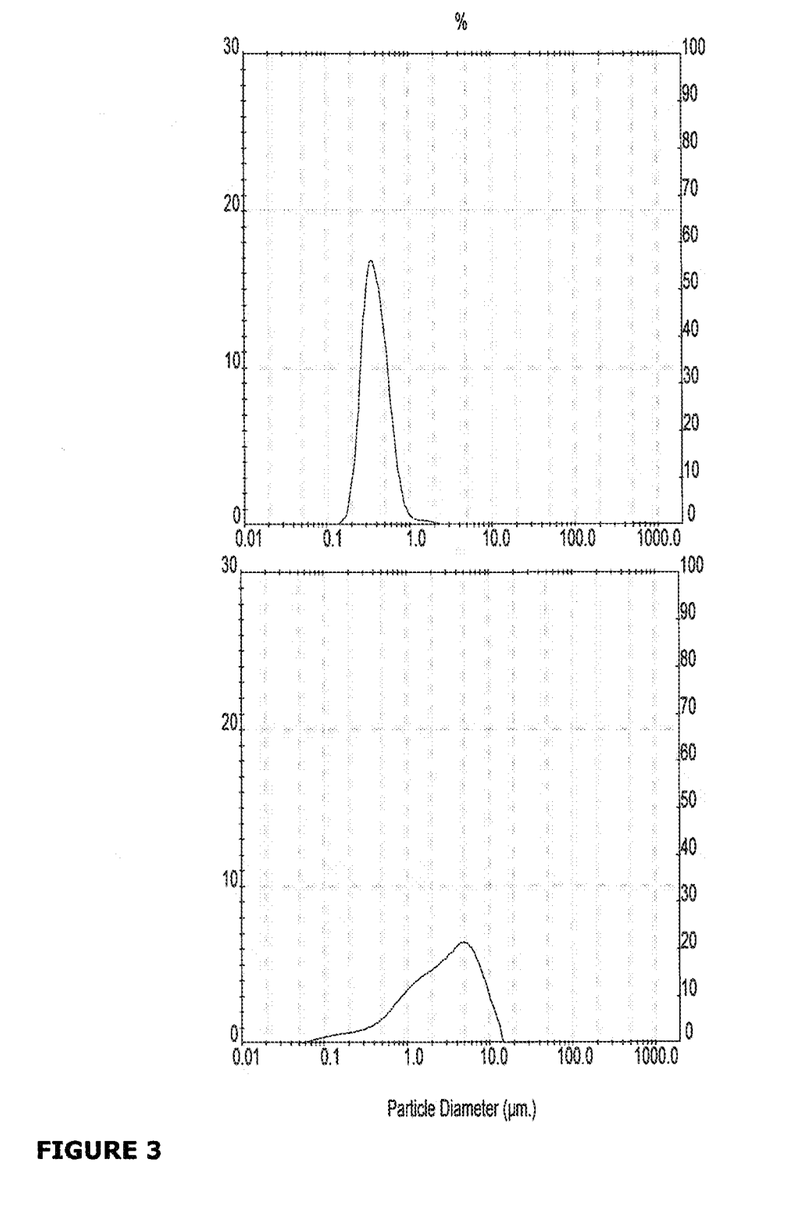
FIG. 3 shows particle size distribution curves for emulsified (top) and milled beta-carotene (bottom).

The average particle size, D(v,0.5), are 0.38 μm and 2.80 μm for the emulsified and milled fraction, respectively. FIG. 3 shows the particle size distributions of the two fractions.

Application results when tested in cheese milk:
Varying ratios of the emulsified beta-carotene and milled, crystalline beta-carotene to find the optimal match annatto in the cheese milk.

Colors studied (and pigment content in parentheses):
Annatto: A-320-WS (1.14%, batch 2971417) from Chr. Hansen
Emulsified beta-carotene (1.48%, batch 2960354—"Emulsified BC II" hereafter)
Milled, crystalline beta-carotene (10.40%, batch 2946953—"Milled BC II" hereafter)

The target sample made with annatto is set at a level of approx. 10 ppm norbixin in 3.5% full-fat UHT milk, which is an unrealistic high dosage for cheese but in this investigation it is used in order to put emphasis on matching color shade and tone in the target. Different levels of Emulsified BC II and Milled BC II are mixed in order to generate a series of ratios to match the appearance of annatto. All tests are carried out without any heat treatment.

A spectrocolorimeter, SPECTRAFLASH SF 450 (Data-Color, Lawrenceville, N.J., USA) with a large aperture (LAV) and calibrated against a white tile, is used for measurements of sup color in reflectance mode.

The ratios of Emulsified BC II and Milled BC II to match annatto in milk are listed in Table 10 together with the pertaining data obtained from measurement of tristimulus color values.

TABLE 10

Tristimulus values L*a*b* for cheese milk added annatto or different ratios of emulsified and milled beta-carotene

| Sample no. | Emulsified BC II (ppm) | Milled BC II (ppm) | L* | a* | b* | C* | H* |
|---|---|---|---|---|---|---|---|
| Annatto (10 ppm A-320) | | | 83.88 | 11.22 | 35.37 | 37.11 | 72.41 |
| 1 | 17.0 | 0.0 | 85.42 | 8.29 | 40.01 | 40.86 | 78.29 |
| 2 | 11.0 | 3.0 | 85.52 | 8.93 | 32.19 | 33.40 | 74.50 |
| 3 | 14.3 | 2.8 | 84.66 | 9.63 | 35.47 | 36.75 | 74.81 |
| 4 | 14.1 | 3.1 | 84.61 | 9.82 | 35.27 | 36.61 | 74.43 |
| 5 | 14.0 | 3.7 | 84.08 | 10.07 | 34.92 | 36.34 | 73.91 |

TABLE 11

Differences relative to annatto (10 ppm A-320) in tristimulus values LCH and E for cheese milk added different ratios of emulsified and milled b-carotene

| Sample no. | Emulsified BC | Milled BC | Ratio | ΔL* | ΔC* | ΔH* | ΔE* | CIE2000 ΔE |
|---|---|---|---|---|---|---|---|---|
| 1 | 17.0 | 0.0 | 0.00 | 1.54 | 3.75 | 4.00 | 5.70 | 3.46 |
| 2 | 11.0 | 3.0 | 0.27 | 1.65 | -3.71 | 1.29 | 4.26 | 2.06 |
| 3 | 14.3 | 2.8 | 0.20 | 0.78 | -0.35 | 1.55 | 1.77 | 1.30 |
| 4 | 14.1 | 3.1 | 0.22 | 0.74 | -0.50 | 1.30 | 1.58 | 1.13 |
| 5 | 14.0 | 3.7 | 0.26 | 0.21 | -0.76 | 0.96 | 1.24 | 0.81 |

In Table 11 crucial parameters for describing color shade and tone are shown relative to that in the standard annatto, 10 ppm A-320-WS. The best match is found for sample no. 5 that exhibit a minimal distance between the color as CIE2000 ΔE is <1, while at the same time color intensity is also very similar ΔC* −0.76. This means that the appearance of 10.3 ppm norbixin can be matched by using 14 ppm Emulsified BC II together with 3.7 ppm of milled beta-carotene.

These findings regarding an optimal ratio of emulsified and milled, crystalline beta-carotene to match norbixin at 10 ppm is expected to be directly proportional when using lower levels of colorant also. This is actually indicated by findings in Example 1 in fresh cheese curd for which total beta-carotene to annatto are in the range 2.1-2.3 for the best matching samples, and if similar calculation is done for sample no. 5 in Example 2 a value of 1.8 is found.

Example 3—Preparation of Gouda 45+ Cheese

Milk

Milk is pasteurized at 72° C. for 20 sec (organic milk, 76-78° C. for 20 sec) and then cooled to 5° C. The content of protein will normally vary from 3.4-3.7% protein. milk is analyzed on the MilkoScan for fat and protein %. The milk is stored in a cooling room until use.

Standardization

The milk for Gouda 45+ production should have a fat content of 3.00% (with protein content of 3.4%) which in the final cheese will result in ~45% fat in dry matter. The fat-to-protein ratio is calculated. The cheese milk is standardized by adding the calculated amounts of cream or skim milk. After standardization the milk is preheated in the heat-exchanger to the pre-ripening temperature of 32° C. and pumped to the cheese vats. A slow agitation (235 rpm) is continued until rennet is dispersed in the milk.

$CaCl_2$ and Saltpeter

Saltpeter is added in a concentration of 0.013% being 20 g per 150 kg milk. $CaCl_2$ can be added to the milk at an amount of 0-20 g per 150 kg milk from a 34% solution if needed.

Culture

As reference culture in the standard Gouda 45+ recipe F-DVS CHN-11 or F-DVS CHN-19 (both obtainable from Chr. Hansen, Denmark) are used with an inoculation of 0.0125% F-DVS CHN-11 (18.75 g per 150 kg) or 0.01% FDVS CHN-19 (15.00 g per 150 kg). Before the rennet addition the culture works for 35 min at 32° C.

Adjuncts

Addition of adjuncts is optional. Adjuncts is added about 5 min before rennet addition. Amount and concentration of adjuncts should be defined, e.g. resulting in $5\times10^6$ cfu/ml in the cheese milk.

Rennet

Rennet CHY-MAX Plus (190 IMCU/mL; obtainable from Chr. Hansen, Denmark) is added at the amount of 0.025% w/w (37.5 g per 150 kg) or CHY-MAX M (950 IMCU/mL; obtainable from Chr. Hansen, Denmark) 5.7 g per 150 kg. The rennet is diluted 3 times its volume in clean cold tap water before use. Agitation (235 rpm) is continued for not more than 1 min after rennet addition and the agitator is removed from the vat. The rennet works for 35 min.

Manufacture of Gouda 45+

Coagulation of the milk normally takes 30-45 min. The coagulum is cut from end to end followed by vertical from end to end in the cheese vat. Then the coagulum is cut vertical from side to side three times down the sides of the vat until cubes of 5 mm are obtained. The curd should be treated very carefully at this stage to minimize losses to the whey. The agitator is returned into the vat and the curd is pre-stirred slowly (350 rpm) for 15-20 min. After 15-20 min 52.5 kg of whey is drained off (35% of the 150 kg cheese milk) and the agitator is then adjusted to a faster level of stirring for 10 min (415 rpm). The scalding is then started by raising the temperature to 38° C. within 10 min. A slow steady and controlled rise in the temperature is required. This is done by sprinkling 45 kg of water (30% of the 150 kg cheesemilk) at a temperature of 47° C.+5° C. energy loss from the sprinkle-aggregate into the cheese vat. Scalding water is prepared using the thermization unit with set temperatures of 85° C. and outlet 57° C.

Temperature control in the cheese vat is set to:

T1 32.0° C. 0 min T2 38.5° C. 10 min

After reaching 38° C., stirring is carried on with a total stirring of 85 min (means 35-45 min. at 38° C.). The curd is examined through the latter stages of agitation to assess progress and small adjustments in the duration of agitation may be made.

Pressing

After 85 min of stirring the agitator is removed and the curd is allowed to settle in the vat. Then the curd is pitched and pre-pressed using the pre-pressing-plates and the hydraulic cylinders to apply a pressure of 1 bar/10 min and 2 bar/15 min to the curd. After pre-pressing the curd is cut in two blocks. The cheese blocks are placed in appropriate molds (30×30 cm) with the same side downwards as during the pre-pressing. The molds are then placed in the pressing unit and pressed for 15 min at 2 bar, 15 min at 3.5 bar and finally 90 min at 5 bar. After end of pressing the height of the cheeses are measured, the cheeses are weight, identified and pH is analyzed. Finally the cheeses are stored in the molds until they reach pH=5.7, and after that directly salted in brine.

Salting

Salting is carried out for 20 hours in a brine of 22% NaCl+0.25% $CaCl_2$ depending of the dimensions of the cheeses, at a temperature of 10-12° C. to reach a salt content of about 1.7% in the final cheeses. It is important that the cheeses are properly separated and submerged during the brine salting to obtain the desired salt content. After salting the cheeses are dried for 1-2 hours before packing.

Coating/Packaging/Storage

The cheeses are dried in the salting room for 1 or 2 days after salting before plastic coating with "Plasticoat AGD 625". The cheeses are stored at 9° C. for 1 week and then plastic coated one time more before storing at 13° C. for 3 weeks. After this the cheeses are vacuumpacked in Cryovac® plastic bags (BK3550) and put into hard plastic boxes (30×30 cm). Finally the cheeses are stored at 9° C. for minimum 2 weeks.

Example 4—Match of Annatto in Production of Gouda 45+ Cheese

To find a match for Annatto (A-320-WS) using standard beta carotene products in cheese Gouda 45+ four vats of Gouda 45+ were made according to the procedure described in Example 3:

Materials & Methods

The following colors were tested:

| Colors | Strength %: | Pigment |
| --- | --- | --- |
| A-320-WS | 1.10 | Annatto |
| Emulsified BC | 1.41 | beta-carotene |
| Milled BC | 10.1 | beta-carotene |

A-320-WS is obtainable from Chr. Hansen, Denmark.

Cheese Process $CaCl_2$ and Color were added 40 and 45 minutes before addition of rennet, respectively

| | |
|---|---|
| Salting | 20 hours in 22% brine at 10° C. |
| Packing | Vacuum bags/Plastic coated |
| Storage | 1 week (w)/9° C.-3 w/13° C.-3 w/9° C.-17 w/4° C. |

No pre-dilution of any of the tested colors before addition into the large cheese vat.

Target cheese composition after 2 weeks of storage:

Fat: ~25.9%. Protein: ~24.2%. Fat in dry matter: ~47.4%. Moisture: ~45.7%.

Procedure

Four vats of Gouda 45+ were made according to ATC procedure. Each vat consisted of 150 kg cheese milk which yielded approximately 16 kg Gouda 45+. Whey from each batch was collected.

| Trial | Color | g/150 L | %-Dose | ppm |
|---|---|---|---|---|
| 1 | No color | — | — | — |
| 2 | A-320-WS | 2.6 | 0.0017% | 0.208 |
| 3 | Emulsified BC + | 2.25 | 0.0015% | 0.212 |
|   | Milled BC | 0.25 | 0.00017% | 0.172 |
| 4 | Emulsified BC + | 2.04 | 0.0014% | 0.192 |
|   | Milled BC | 0.29 | 0.00019% | 0.192 |

Instruments

Spectrocolorimeter: SPECTRAFLASH SF 450 (Data-Color)

MilkoScan (Foss)

Cheese equipment in ATC

Freeze dryer: Heto CD10. Temperature 32° C., Pressure 0.5 mBar.

Color Evaluations

Color measurements were performed on the DataColor SF450, LAV opening (calibrated to a white tile). The measurements were complemented by visual evaluations of the samples during the stability trials.

Stability Test

The L*a*b* values were determined by DataColor SF450 over approximately 23 weeks. Determinations were made at approx D3 (initially), Week 6, Week 12 and Week 23. A piece of the cheese was cut and a comparison of the 4 cheeses was made in a picture. Following a new slice of each piece was cut immediately before each reading. Each determination is the average of approximately 6 readings.

Results & Discussion

Composition in cheese milk: 3.09% Fat-3.49% Protein-4.68% Lactose-9.14% SNF.

TABLE 12

L*a*b* Values of cheese milk

| Trial | L* | a* | b* | C* | H* | DL* | DC* | DH* | DE* | DE* CMC | CIE2000 DE |
|---|---|---|---|---|---|---|---|---|---|---|---|
| 2 | 88.71 | −0.42 | 13.46 | 13.47 | 91.77 | | | | | | |
| 3 | 88.88 | −0.30 | 12.70 | 12.71 | 91.34 | 0.17 | −0.76 | −0.10 | 0.79 | 0.57 | 0.51 |
| 4 | 88.83 | −0.28 | 12.57 | 12.57 | 91.27 | 0.12 | −0.90 | −0.11 | 0.91 | 0.67 | 0.59 |
| 1 | 89.49 | −1.52 | 11.43 | 11.54 | 97.58 | 0.78 | −1.93 | 1.26 | 2.44 | 2.09 | 2.06 |

The L*a*b* values were determined by DataColor Spectroflash SF450

Figure 4:
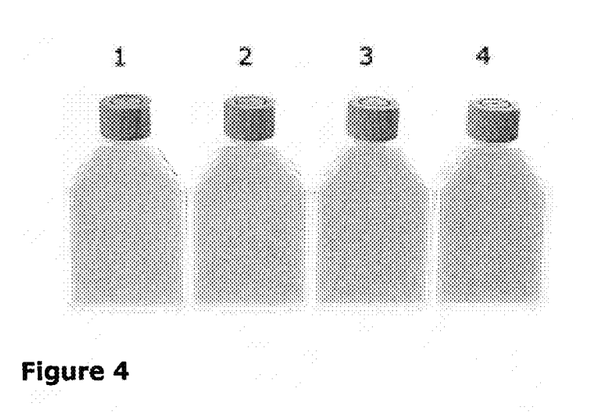
FIG. 4 shows 4 samples of cheese milk. 1. No color; 2. A-320-WS (0.21 ppm); 3. Emulsified BC (0.21 ppm)+Milled BC (0.17 ppm); 4. Emulsified BC (0.19 ppm)+Milled BC (0.19 ppm).

In the cheese milk it can be observed that there is hardly any difference in the different combinations of the Emulsified BC and the Milled BC. All tested combinations of the BC have slightly lower chroma than the appearance of 0.0017% A-320-WS in cheese milk. See FIG. 4.

TABLE 13

Composition in Whey

| Color | % - Fat | % - Protein | % - LAC | % - SNF |
|---|---|---|---|---|
| No Color | 0.39 | 0.87 | 4.32 | 6.02 |
| A-320-WS | 0.36 | 0.96 | 4.71 | 6.57 |
| Emulsified BC + Milled BC | 0.41 | 0.97 | 4.71 | 6.58 |
| Emulsified BC + Milled BC | 0.39 | 0.97 | 4.71 | 6.57 |

The whey compositions are similar in all the cheeses.

Samples of all the whey were freeze-dried into powders for further testing of color content.

TABLE 14

L*a*b* Values of Whey

| Trial | L* | a* | b* | C* | H* | DL* | DC* | DH* | DE* | DE* CMC | CIE2000 DE |
|---|---|---|---|---|---|---|---|---|---|---|---|
| 2 | 58.09 | −4.47 | 9.86 | 10.83 | 114.37 | | | | | | |
| 3 | 56.81 | −3.88 | 10.47 | 11.17 | 110.35 | −1.28 | 0.34 | −0.77 | 1.53 | 1.05 | 1.46 |

TABLE 14-continued

L*a*b* Values of Whey

| Trial | L* | a* | b* | C* | H* | DL* | DC* | DH* | DE* | DE* CMC | CIE2000 DE |
|---|---|---|---|---|---|---|---|---|---|---|---|
| 4 | 58.58 | −4.06 | 10.65 | 11.40 | 110.86 | 0.49 | 0.57 | −0.68 | 1.02 | 0.91 | 0.92 |
| 1 | 58.79 | −4.16 | 10.32 | 11.12 | 111.95 | 0.70 | 0.30 | −0.46 | 0.89 | 0.64 | 0.82 |

The L*a*b* values were determined by DataColor Spectroflash SF450

Figure 5:
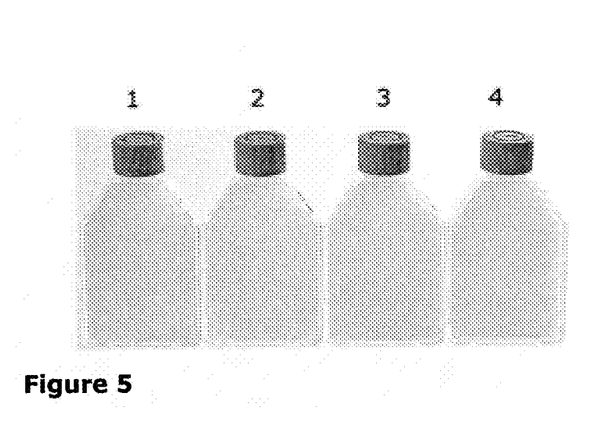
FIG. 5 depicts 4 samples of whey. 1. No color; 2. A-320-WS (0.21 ppm); 3. Emulsified BC (0.21 ppm)+Milled BC (0.17 ppm); 4. Emulsified BC (0.19 ppm)+Milled BC (0.19 ppm).

The most colorful whey is from the cheese added 0.0017% A-320-WS. There is hardly any difference in the tested levels of BC products. FIG. 5 shows that the added annatto to the cheese milk is not retained completely in the cheese curd and by consequence it is coloring the whey.

TABLE 15

Pigment content, annatto or beta-carotene, in the whey powder and liquid whey

| Color | cheese milk - pigment conc. (ppm) | whey powder - pigment conc. (ppm) | liquid whey - pigment conc. (ppm) | pigment transferred to whey (%) |
|---|---|---|---|---|
| No Color* | — | 0.42** | 0.030 | 14 |
| A-320-WS | 0.208 | 0.80** | 0.057 | 27 |
| Emulsified BC + Milled BC | 0.212 + 0.172 = 0.384 | 1.00 | 0.072 | 11 |

TABLE 15-continued

Pigment content, annatto or beta-carotene, in the whey powder and liquid whey

| Color | cheese milk - pigment conc. (ppm) | whey powder - pigment conc. (ppm) | liquid whey - pigment conc. (ppm) | pigment transferred to whey (%) |
|---|---|---|---|---|
| Emulsified BC + Milled BC | 0.192 + 0.192 = 0.384 | 0.93 | 0.067 | 10 |
| Cheese milk | — | 1.70 | 0.215 | — |

*The natural presence of beta-carotene in cheese milk is 0.42 ppm beta-carotene in dried whey powder and after correcting for concentration factor it means that the liquid whey fraction contains 0.030 ppm beta-carotene. These numbers correspond to a relative transfer of 14% originating from natural beta-carotene content in cheese milk. This background value has been used to correct transfer values for samples added beta-carotene colorants in the cheese milk. In contrast, cheese added annatto is not corrected as analysis method is specific for norbixin and because milk does not naturally contain norbixin.
**Method of analysis is based on HPLC techniques using pure components, norbixin or beta-carotene (sum of isomers) as standards. Analyses are performed externally at an accredited Analysis Laboratory.

Annatto or beta-carotene determinations were carried out for the freeze-dried whey powders, and subsequently the content in liquid whey was calculated based on mass balance data.

Cheese Storage

Cheese ripening was followed for 24 weeks with the following storage profile:
1w/9° C.-3w/13° C.-3w/9° C.-17w/4° C.

TABLE 16

L*a*b* values comparison of the cheeses at Day 03

| Trial | L* | a* | b* | C* | H* | DL* | DC* | DH* | DE* | DE* CMC | CIE2000 DE |
|---|---|---|---|---|---|---|---|---|---|---|---|
| 2 | 88.38 | 6.60 | 26.53 | 27.34 | 76.03 | | | | | | |
| 3 | 88.33 | 5.91 | 25.45 | 26.12 | 76.92 | −0.05 | −1.22 | 0.41 | 1.29 | 0.76 | 0.67 |
| 4 | 88.35 | 6.04 | 25.10 | 25.82 | 76.47 | −0.04 | −1.52 | 0.20 | 1.54 | 0.82 | 0.72 |
| 1 | 89.77 | 2.91 | 23.32 | 23.50 | 82.89 | 1.39 | −3.84 | 3.03 | 5.08 | 3.74 | 3.48 |

Comments (before ripening, Day 04 - initially):
Lightness (L*) is similar among the colored cheeses. All tested combinations of the BC standard products have initially lower chroma which indicates a less intense color and also a more yellow hue values of cheeses with BC than the cheese with annatto alone.

TABLE 17

L*a*b* values comparison of the cheeses at Week 06

| Trial | L* | a* | b* | C* | H* | DL* | DC* | DH* | DE* | DE* CMC | CIE2000 DE |
|---|---|---|---|---|---|---|---|---|---|---|---|
| 2 | 82.32 | 8.81 | 35.30 | 36.38 | 75.99 | | | | | | |
| 3 | 82.91 | 8.06 | 33.75 | 34.70 | 76.57 | 0.59 | −1.68 | 0.36 | 1.82 | 0.85 | 0.81 |
| 4 | 82.75 | 8.31 | 33.67 | 34.68 | 76.14 | 0.43 | −1.70 | 0.09 | 1.75 | 0.79 | 0.72 |
| 1 | 84.74 | 3.99 | 30.42 | 30.68 | 82.54 | 2.43 | −5.70 | 3.82 | 7.28 | 4.38 | 4.13 |

The same differences observed at the initial evaluation are also seen after six weeks.

TABLE 18

L*a*b* values comparison of the cheeses at Week 12

| Trial | L* | a* | b* | C* | H* | DL* | DC* | DH* | DE* | DE* CMC | CIE2000 DE |
|---|---|---|---|---|---|---|---|---|---|---|---|
| 2 | 82.16 | 8.95 | 35.42 | 36.53 | 75.82 | | | | | | |
| 3 | 81.92 | 8.37 | 34.42 | 35.42 | 76.33 | −0.24 | −1.11 | 0.32 | 1.18 | 0.59 | 0.52 |
| 4 | 81.89 | 8.52 | 34.32 | 35.36 | 76.05 | −0.28 | −1.17 | 0.15 | 1.21 | 0.55 | 0.50 |
| 1 | 83.90 | 4.12 | 30.49 | 30.77 | 82.30 | 1.74 | −5.76 | 3.79 | 7.12 | 4.34 | 3.97 |

The same differences observed at the initial evaluation are also seen after twelve weeks.

TABLE 19

L*a*b* values comparison of the cheeses at Week 23

| Trial | L* | a* | b* | C* | H* | DL* | DC* | DH* | DE* | DE* CMC | CIE2000 DE |
|---|---|---|---|---|---|---|---|---|---|---|---|
| 2 | 81.96 | 8.79 | 34.76 | 35.85 | 75.80 | | | | | | |
| 3 | 82.27 | 8.28 | 34.12 | 35.11 | 76.35 | 0.31 | −0.74 | 0.34 | 0.87 | 0.47 | 0.44 |
| 4 | 82.77 | 8.26 | 33.41 | 34.42 | 76.11 | 0.81 | −1.43 | 0.19 | 1.66 | 0.74 | 0.79 |
| 1 | 84.73 | 4.02 | 30.72 | 30.99 | 82.55 | 2.77 | −4.87 | 3.92 | 6.84 | 4.31 | 4.13 |

The same differences observed at the initial evaluation are also seen after twenty-four weeks. Lightness (L*) is similar among the colored cheeses. All tested combinations of the BC standard products have slightly lower chroma which indicates a less intense color and also a more yellow hue values of cheeses with BC than the cheese with Annatto alone. Both BC combinations in cheese are close to the appearance of the Annatto in cheese.

Evolution of the L*a*b* Values after 23 Weeks of Stability Study

During ripening, body color of Gouda cheese 45+ was evaluated by spectrocolorimetric analyses.

It was found that lightness (L*) decreases with increasing maturation time. This decrease in L* is associated to changes in the cheese matrix during ripening. Brightness (Chroma) was found to increase with increasing maturation time. Cheeses become more intense or the color becomes more vivid up until week 12.

Figure 6:
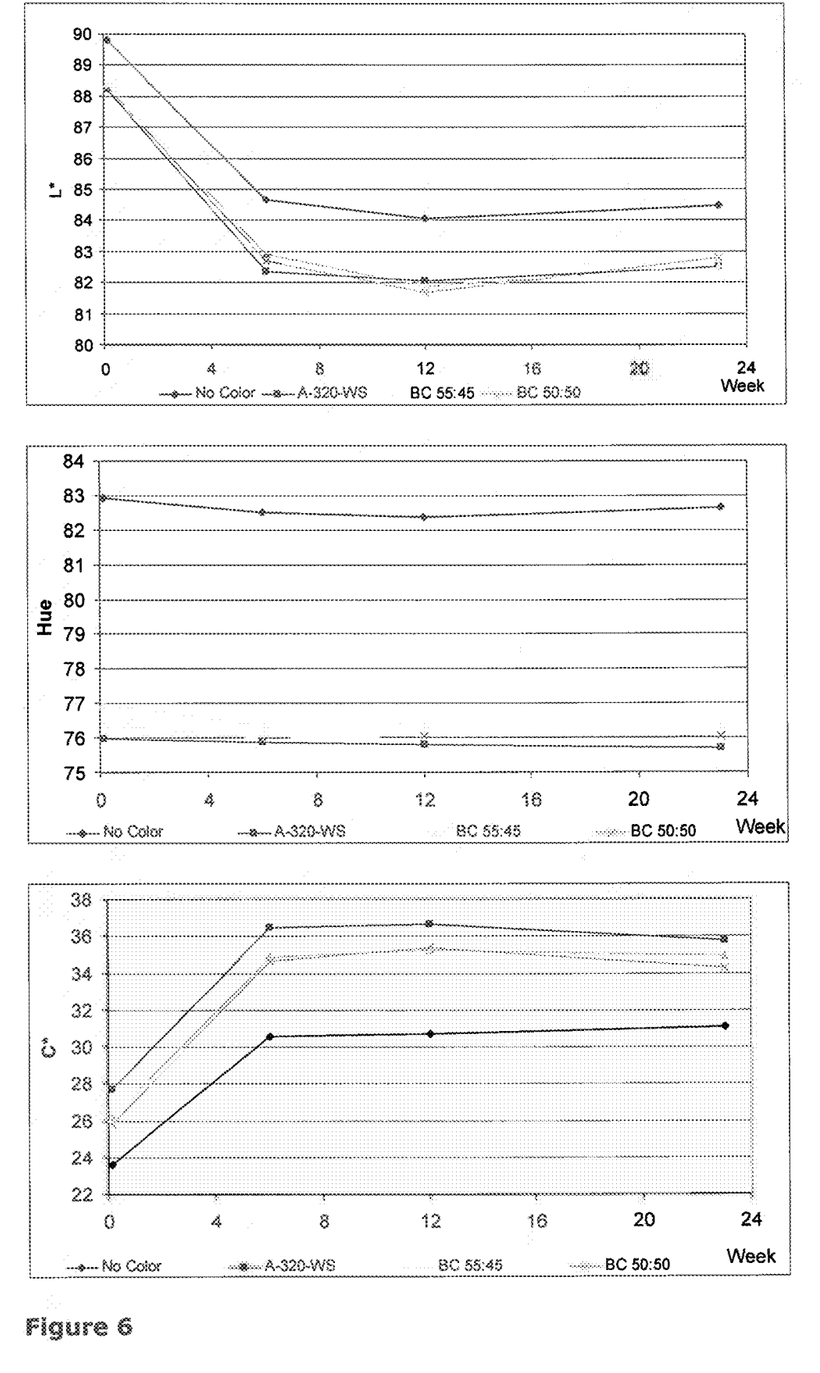
FIG. 6 depicts the evolution of L*a*b* values over 23 weeks of stability study. The top graph shows the lightness (L*), the middle graph shows the hue and the bottom graph shows the brightness (chroma; C*).

The hue of the cheese body shifts towards a slightly more orange color in the first stage of ripening (6 weeks). Following the hues increase slightly. See FIG. 6.

Visual Evaluation of the Cheeses at Week 23

Figure 7:
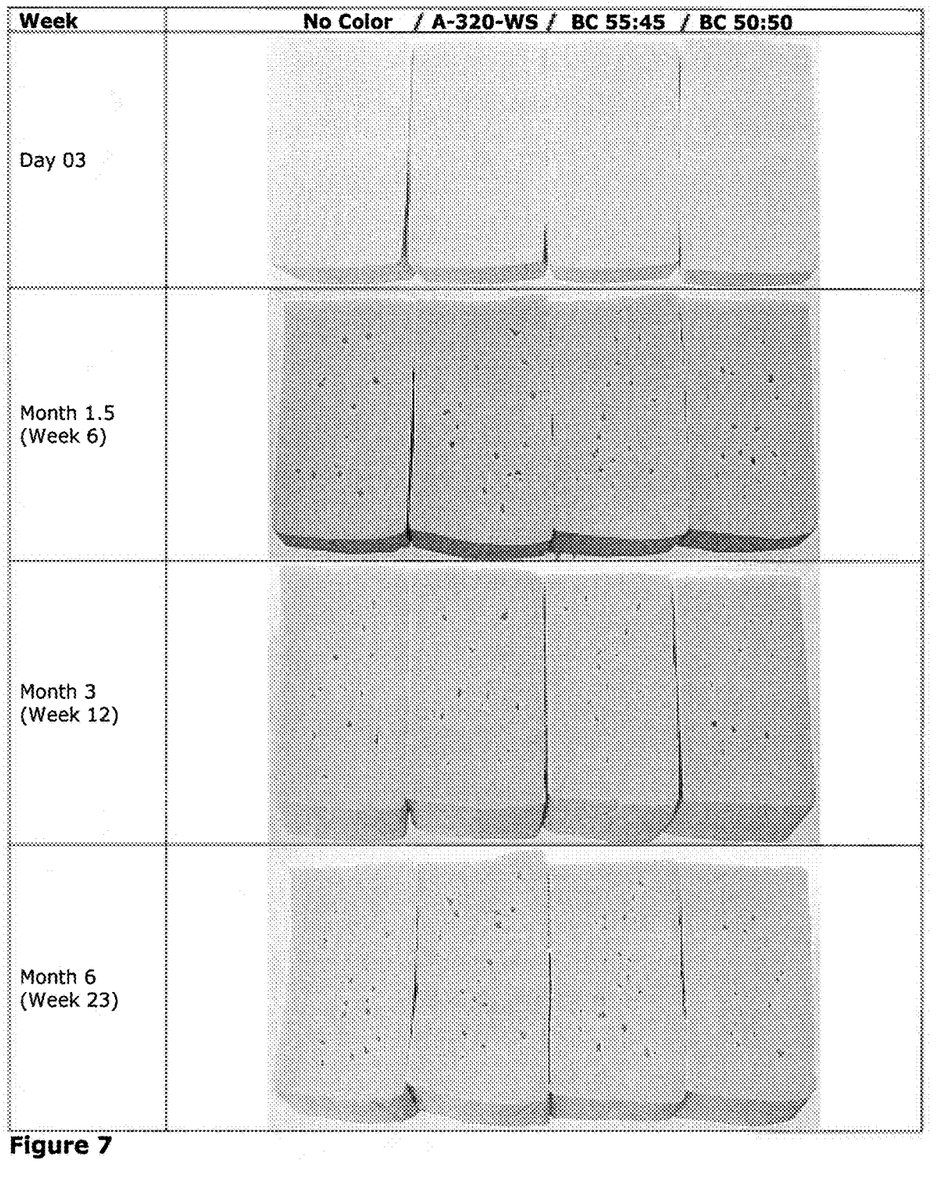
FIG. 7 shows slices of Gouda 45+ cheeses over 23 weeks of stability study. Day 03, young cheeses ready for maturation; Month 1.5, cheeses ready for consumption; Month 3 cheeses ready for consumption; Month 6, mature cheeses ready for consumption.

It is possible to see a slightly difference on the cheeses colored with different combinations of the BC standard product compared to the cheese colored with annatto. However, both combinations are very close to the appearance of the cheese with annatto. See FIG. 7.

REFERENCES

GB 2248170 (Hoffmann La-Roche AG)
WO 99/07233 (Rhodia Inc.)
WO 2002/41711 (Unilever N.V.)
WO 2007/009601 (DSM IP Assets B.V.)
WO 2008/110225 (DSM IP Assets B.V.)
WO 2010/069889 (Cybercolors Ltd.)
WO 2010/112406 (BASF SE)
US 2001/0046546 (Ernster)
Carrie, M. (1938). Journal of Dairy Research 9, pp. 72-79.
McDonough, F. E., Hargrove, R. E., Tittsler, R. P. (1968). Journal of Dairy Science 51(3), pp. 471-472.
Croissant, A. E., Kang, E. J., Campbell, R. E., Bastian, E., Drake, M. A. (2009). Journal of Dairy Science 92(12), pp. 5917-5927.
Noziere, P., Graulet, B., Lucas, A., Martin, B., Grolier, P., Doreau, M. (2006). Animal Feed Science and Technology 131, pp. 418-450.
Lück, H.; Downes, T. E. H. (1972). South African Journal of Dairy Technology 4(4), pp. 207-213.
Lück, H. (1973). South African Journal of Dairy Technology 5(4), pp. 181-185.
Chapman, H. R. et al. (1980). Journal of the Society of Dairy Technology 33(4), pp. 162-164.
Kang, E. J.; Campbell, R. E.; Bastian, E.; Drake, M. A. (2010). Journal of Dairy Science 93(9), pp. 3891-3901.

The invention claimed is:

1. A liquid coloring composition comprising:
   (a) an oil-in-water emulsion comprising a carotenoid dissolved in an oil phase, wherein the oil phase is emulsified in an aqueous phase using a suitable emulsifier and wherein the oil phase is present in an amount of between 5% (w/w) to 40% (w/w) of the oil-in-water emulsion; and
   (b) a formulation of water dispersible carotenoid particles encapsulated with a suitable hydrocolloid, wherein the hydrocolloid is present in an amount of at least 0.5% (w/w) of the formulation;
   wherein the ratio of (a):(b) is from 1:10 to 10:1, the carotenoid content of each of (a) and (b) is at least 1% (w/w) of the resulting liquid coloring composition, and the total carotenoid content of (a) and (b) is up to 15% (w/w) of the resulting liquid coloring composition.

2. The liquid coloring composition according to claim 1, wherein the oil phase is present in an amount of between 15% (w/w) to 25% (w/w) of (a).

3. The liquid coloring composition according to claim 1, wherein the carotenoid of (a) is the same as the carotenoid of (b) and is selected from the group consisting of beta-carotene, alpha-carotene, gamma-carotene, zeaxanthin, lutein, cis/trans isomers thereof and combinations thereof.

4. The liquid coloring composition according to claim 3, wherein the carotenoid is beta-carotene.

5. The liquid coloring composition according to claim 4, wherein the emulsifier is selected from the group consisting of lecithin, caseinate and a combination thereof.

6. The liquid coloring composition according to claim 4, wherein the hydrocolloid is selected from the group consisting of non-modified starch, modified starch, milk protein, pea protein, beet pectin and combinations thereof.

7. The liquid coloring composition according to claim 4, wherein the hydrocolloid is present in an amount of at least 5% (w/w) of the formulation.

8. A method for preparing a liquid coloring composition comprising the steps of:
(a) preparing an oil-in-water emulsion of a dissolved carotenoid using a suitable emulsifier by:
   (i) preparing an aqueous phase;
   (ii) preparing an oil phase by heating a fat comprising the carotenoid to a temperature suitable for dissolving the carotenoid; and
   (iii) mixing the oil phase in the aqueous phase;
(b) preparing a formulation of carotenoid particles encapsulated in a suitable hydrocolloid by milling carotenoid particles in the presence of a suitable hydrocolloid; and
(c) mixing the oil-in-water emulsion of (a) with the encapsulated carotenoid particle formulation of (b) in a ratio of from 1:10 to 10:1,
wherein the carotenoid content of each of (a) and (b) is at least 1% (w/w) of the resulting liquid coloring composition and the total carotenoid content of (a) and (h) is up to 15% (w/w) of the resulting liquid composition.

9. The method according to claim 8, wherein in (a)(ii) the temperature suitable for dissolving the carotenoid is between 140° C. to 160° C.

10. A method of coloring cheese comprising the steps of:
(a) adding a starter culture, rennet and the liquid coloring composition according to claim 1 to milk to obtain a colored cheese milk;
(b) incubating the mixture under conditions favorable to the generation of curd and Whey fractions; and
(c) separating the curds from the whey to obtain colored curds,
(d) preparing colored cheese from the colored curds.

11. A food product, a beverage, an animal feed, a cosmetic or a drug comprising the liquid coloring composition according to claim 1.

12. A food product according to claim 11, wherein the food product is a cheese.

13. A method of coloring a food product, a beverage, an animal feed, a cosmetic or a drug, comprising adding the liquid coloring composition according to claim 1 to the food product, beverage, animal feed, cosmetic or drug.

14. The method according to claim 13, wherein the food product is a cheese.

15. The method according to claim 10, wherein, in the liquid coloring composition, the carotenoid of (a) is the same as the carotenoid of (b) and is selected from the group consisting of beta-carotene, alpha-carotene, gamma-carotene, zeaxanthin, lutein, cis/trans isomers thereof and combinations thereof.

16. The method according to claim 15, wherein, in the liquid coloring composition, the carotenoid of (a) is the same as the carotenoid of (b) and is beta-carotene.

17. The method according to claim 15, wherein, in the liquid coloring composition, the ratio of (a):(b) is from 1:5 to 5:1.

18. The liquid coloring composition according to claim 1, wherein the ratio of (a):(b) is from 1:5 to 5:1.

19. The method according to claim 8, wherein in (c), the oil-in-water emulsion of (a) is mixed with the encapsulated carotenoid particle formulation of (b) in a ratio of from 1:5 to 5:1.

* * * * *

UNITED STATES PATENT AND TRADEMARK OFFICE
CERTIFICATE OF CORRECTION

PATENT NO. : 10,660,346 B2
APPLICATION NO. : 14/123723
DATED : May 26, 2020
INVENTOR(S) : Moeller et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 563 days.

Signed and Sealed this
Twenty-seventh Day of December, 2022

Katherine Kelly Vidal
*Director of the United States Patent and Trademark Office*